United States Patent
Whitcup et al.

(10) Patent No.: US 12,156,873 B2
(45) Date of Patent: Dec. 3, 2024

(54) COMPOSITION FOR TREATING OCULAR HYPEREMIA AND A METHOD FOR TREATING OCULAR HYPEREMIA WITH THE SAME

(71) Applicant: ADS Therapeutics LLC, Irvine, CA (US)

(72) Inventors: Scott Whitcup, Irvine, CA (US); Rong Yang, Irvine, CA (US); Jinsong Ni, Irvine, CA (US)

(73) Assignee: ADS Therapeutics LLC, Irvine, CA (US)

( * ) Notice: Subject to any disclaimer, the term of this patent is extended or adjusted under 35 U.S.C. 154(b) by 838 days.

(21) Appl. No.: 17/057,886

(22) PCT Filed: May 23, 2019

(86) PCT No.: PCT/US2019/033692
§ 371 (c)(1),
(2) Date: Nov. 23, 2020

(87) PCT Pub. No.: WO2019/226864
PCT Pub. Date: Nov. 28, 2019

(65) Prior Publication Data
US 2021/0228574 A1    Jul. 29, 2021

Related U.S. Application Data

(60) Provisional application No. 62/676,437, filed on May 25, 2018.

(51) Int. Cl.
*A61K 31/498* (2006.01)
*A61K 9/00* (2006.01)
(Continued)

(52) U.S. Cl.
CPC .......... *A61K 31/498* (2013.01); *A61K 9/0014* (2013.01); *A61K 9/06* (2013.01);
(Continued)

(58) Field of Classification Search
CPC ...... A61K 31/498; A61K 31/496; A61P 27/02
See application file for complete search history.

(56) References Cited

U.S. PATENT DOCUMENTS

| | | | |
|---|---|---|---|
| 8,513,247 B2 | 8/2013 | Graeber et al. | |
| 2006/0173060 A1* | 8/2006 | Chang ................ | A61K 31/4166 424/490 |

(Continued)

FOREIGN PATENT DOCUMENTS

| | | |
|---|---|---|
| WO | WO 2001027081 | 4/2001 |
| WO | WO 2007038453 | 4/2007 |

(Continued)

OTHER PUBLICATIONS

Rodrigues et al. "Neovascular glaucoma: a review,", International Journal of Retina and Vitreous, 2016, vol. 2,:26 (Year: 2016).*

(Continued)

*Primary Examiner* — San Ming R Hui
(74) *Attorney, Agent, or Firm* — Fish & Richardson P.C.

(57) ABSTRACT

A composition for use in the treatment of ocular hyperemia includes an anti-angiogenic agent and an α adrenergic receptor agonist. A method for treating ocular hyperemia for a patient includes inhibiting a plurality of kinase receptors of the patient with an MKI; and activating α adrenergic receptor of the patient with an agonist of the receptor.

7 Claims, 1 Drawing Sheet

(51) Int. Cl.
| | |
|---|---|
| *A61K 9/06* | (2006.01) |
| *A61K 9/08* | (2006.01) |
| *A61K 9/107* | (2006.01) |
| *A61K 31/496* | (2006.01) |
| *A61K 47/26* | (2006.01) |
| *A61K 47/34* | (2017.01) |
| *A61K 47/36* | (2006.01) |
| *A61P 27/02* | (2006.01) |

(52) U.S. Cl.
CPC ............... *A61K 9/08* (2013.01); *A61K 9/107* (2013.01); *A61K 31/496* (2013.01); *A61K 47/26* (2013.01); *A61K 47/34* (2013.01); *A61K 47/36* (2013.01); *A61P 27/02* (2018.01)

(56) References Cited

U.S. PATENT DOCUMENTS

| | | |
|---|---|---|
| 2010/0029660 A1 | 2/2010 | Horn et al. |
| 2015/0125539 A1 | 5/2015 | Popov et al. |
| 2017/0105932 A1 | 4/2017 | Ambati et al. |
| 2017/0209368 A1 | 7/2017 | Ni |

FOREIGN PATENT DOCUMENTS

| | | | |
|---|---|---|---|
| WO | WO-2016200688 A1 * | 12/2016 | ............... A61F 9/00 |
| WO | 2017/062948 A1 | 4/2017 | |
| WO | 2017210132 A1 | 12/2017 | |
| WO | 2018218116 A1 | 11/2018 | |

OTHER PUBLICATIONS

Kampougeris, G et al. Intraocular Pressure Rise After Anti-VEGF Treatment: Prevalence, Possible Mechanisms and Correlations. Journal of Current Glaucoma Practice. Jan.-Apr. 2013, vol. 7, No. 1: pp. 19-24.

Barar, J. et al. Advanced Drug Delivery and Targeting Technologies for the Ocular Diseases. BioImpacts. Mar. 30, 2016, vol. 6, No. 1: pp. 49-67.

ClinicalTrial.gov NCT03533244: "A study of the response to AG-86893 in patients with pterygium hyperemia" May 23, 2018, pp. 1-7, XP055884166.

Hurmeric V. et al., "single and multiple injections of subconjuctival ranibizumab for early, recurrent pterygium" Clinical Ophthalmology, vol. 7, Jan. 1, 2013, pp. 467-473, XP055884597.

Teng C.C. et al. "Effect of subconjunctival bevacizumab on primary pterygium" Cornea: The Journal of Cornea and External Disease, vol. 28, No. 4, May 1, 2009, pp. 468-470, XP055884603.

El Chehab H et al., "Effect of topical pressure-lowering medication on prevention of intraocular pressure spikes after intravitreal injection" European Journal of Ophthalmology, vol. 23, No. 3, Nov. 15, 2021, pp. 277-283, XP055883931.

Cantor LB et al., "brimonidine in the treatment of glaucoma and ocular hypertension" Therapeutics and Clinical Risk Management, vol. 2, No. 4, Dec. 1, 2006, pp. 337-346, XP055476314.

Cronau et al., " Diagnosis and Management of Red Eye in Primary Care," American Family Physician, Jan. 2010, 81(2):137-144.

International Preliminary Report on Patentability in PCT Appln. No. PCT/US2019/033692, mailed on Dec. 10, 2020, 9 pages.

International Search Report and Written Opinion in PCT Appln. No. PCT/US2019/033692, mailed on Jul. 26, 2019, 11 pages.

Ko et al., "Inhibition of Corneal Neovascularization by Subconjunctival and Topical Bevacizumab and Sunitinib in a Rabbit Model," Cornea, May 2013; 32(5):689-695.

Lucentis (ranibizumab injection), package insert. South San Francisco, CA: Genentech, Inc., 2014.

Pérez-Santonja et al., "Inhibition of corneal neovascularization by topical bevacizumab (Anti-VEGF) and sunitinib (Anti-VEGF and Anti-PDGF) in an animal model," American Journal of Ophthalmology, Oct. 2010, 150(4):519-528.e1.

Torkildsen et al., "Evaluation of Efficacy and Safety of Brimonidine Tartrate Ophthalmic Solution, 0.025% for Treatment of Ocular Redness," Current Eye Research, Jan. 2018,43(1):43-51.

* cited by examiner

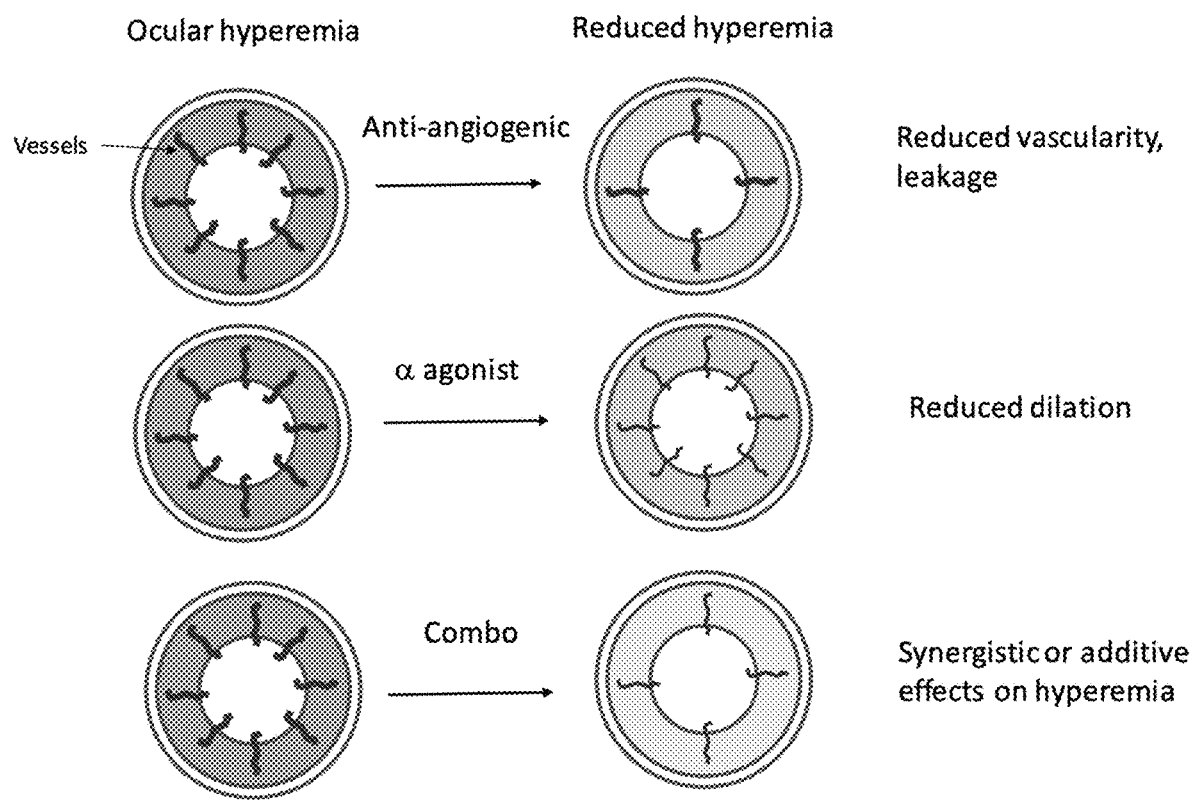

COMPOSITION FOR TREATING OCULAR HYPEREMIA AND A METHOD FOR TREATING OCULAR HYPEREMIA WITH THE SAME

This application is the National Stage Application of PCT/US2019/033692, filed on May 23, 2019, which claims priority to U.S. Provisional Application No. 62/676,437, filed on May 25, 2018, which is incorporated by reference for all purposes as if fully set forth herein.

FIELD OF THE INVENTION

The present invention relates to a composition for treating ocular hyperemia and a method for treating ocular hyperemia with the same, more specifically, a composition including a combination of an anti-angiogenesis agent and an α adrenergic receptor agonist for treating ocular hyperemia and a method for treating ocular hyperemia with the same.

BACKGROUND OF THE INVENTION

Hyperemia

Hyperemia (redness) is a condition caused by abnormalities associated with the blood vessels at affected locations, often on the eye or skin. Excess vessel growth and increased vascularity is one of the major causes. In addition, abnormal vessel dilation or leakage often lead to hyperemia. Many diseases and conditions, such as inflammation, can induce hyperemia.

Treatment of Hyperemia

Hyperemia can be reduced by treating the underlying causes, for example, using antibiotics to treat acute bacterial conjunctivitis. Hyperemia can also be treated by modulating the abnormalities associated with blood vessels at the affected area.

There is a need for an effective and safe treatment for hyperemia, particularly ocular hyperemia, due to the sensitive nature of eyes.

SUMMARY OF THE INVENTION

In one embodiment, the present invention provides a composition for use in the treatment of ocular hyperemia. The composition includes an anti-angiogenic agent and an α adrenergic receptor agonist.

In another embodiment, the anti-angiogenic agent is a multi-kinase inhibitor (MKI) that inhibits one or more selected from the group consisting of Vascular Endothelial Growth Factor Receptors (VEGFR) 1, 2, and 3 and Platelet-derived Growth Factor Receptor (PDGFR) α, β and Lyn.

In another embodiment, the MKI is selected from the group consisting of afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, linifanib, motesanib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, and vemurafenib; and the MKI is preferably nintedanib or axitinib.

In another embodiment, the anti-angiogenic agent is a biological agent that binds to VEGF to block the signal transduction of VEGF.

In another embodiment, the biological agent is selected from the group consisting of bevacizumab, ranibizumab, ramucirumab, aflibercept, and conbercept.

In another embodiment, the α adrenergic receptor agonist is selected from the group consisting of naphazoline, tetrahydrozoline, oxymetazoline, methoxamine, phenylephrine, xylometazoline, oxedrine, Apraclonidine, mivaZerol, clonidine, brimonidine, alpha methyl dopa, guanfacine, dexemeditomidine, (+)-(S)-4-1-(2,3-dimethyl-phenyl)-ethyl-1,3-dihydro-imidazole-2-thione, 1-(imidazolidin-2-yl)iminolindazole, methoxamine, phenylephrine, tizanidine, xylazine, guanabenz, and amitraz.

In another embodiment, the α adrenergic receptor agonist is an α2-adrenergic receptor agonist that is selective for α2-adrenergic receptors.

In another embodiment, the α2-adrenergic receptor agonist is selected from the group consisting of brimonidine, apraclonidine, mivaZerol, clonidine, alpha methyl dopa, guanfacine, dexemeditomidine, (+)-(S)-4-1-(2,3-dimethyl-phenyl)-ethyl-1,3-dihydro-imidazole-2-thione, 1-(imidazolidin-2-yl)iminolindazole, methoxamine, phenylephrine, tizanidine, xylazine, guanabenz, and amitraz; and the α2-adrenergic receptor agonist is preferably brimonidine.

In another embodiment, the composition includes 0.001%-1% nintedanib and 0.001%-1% brimonidine; preferably 0.01%-0.5% nintedanib and 0.01%-0.5% brimonidine; preferably 0.1%-0.3% nintedanib and 0.01%-0.05% brimonidine; more preferably 0.2% nintedanib and 0.025% brimonidine.

In another embodiment, the composition further includes one or more pharmaceutically acceptable excipients selected from stabilizers, surfactants, polymer base carriers, gelling agents, organic co-solvents, pH active components, osmotic active components and with or without preservatives.

In another embodiment, the composition is a topical ocular formulation, an ointment, a gel, a sustained release semi-solid formulation, a sustained release solid formulation or an ocular implant; and the topical ocular formulation is preferably an aqueous solution, a suspension, or an emulsion.

In another embodiment, the sustained release semi-solid formulation, the sustained release solid formulation or the ocular implant comprises a biodegradable polymer selected from the group consisting of polylactic acid (PLA), poly lactic-co-glycolic acid (PLGA) and polylactic acid poly lactic-co-glycolic acid copolymers.

In one embodiment, the present invention provides a method for treating ocular hyperemia for a patient. The method includes inhibiting a plurality of kinase receptors of the patient with an MKI; and activating α adrenergic receptor of the patient. The kinase receptors are selected from the group consisting of VEGFR 1, 2, and 3, and PDGFR a, B, and Lyn, and preferably VEGFR1, 2, or 3.

In another embodiment, the MKI is selected from the group consisting of afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, linifanib, motesanib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, and vemurafenib; and the anti-angiogenic agent is preferably nintedanib or axitinib; and activating the α-adrenergic receptor comprises administering an α adrenergic receptor agonist selected from the group consisting of naphazoline, tetrahydrozoline, oxymetazoline, methoxamine, phenylephrine, xylometazoline, oxedrine, Apraclonidine, mivaZerol, clonidine, brimonidine, alpha methyl dopa, guanfacine, dexemeditomidine, (+)-(S)-4-1-(2,3-dimethyl-phenyl)-ethyl-1,3-dihydro-imidazole-2-thione, 1-(imidazo-lidin-2-yl)iminolindazole, methoxamine, phenylephrine, tizanidine, xylazine, guanabenz, and amitraz; and the α-adrenergic receptor agonist is preferably brimonidine.

In another embodiment, the anti-angiogenic agent and the α-adrenergic receptor agonist are administered to an affected eye in the form of a topical ocular formulation, an ointment, a gel, a sustained release semi-solid formulation, a sustained release solid formulation or an ocular implant.

In another embodiment, the sustained release semi-solid formulation, the sustained release solid formulation, or the ocular implant is injected into the affected eye.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows the treatment of ocular hyperemia with an anti-angiogenic agent, an α adrenergic receptor agonist, and a combination of an anti-angiogenic agent and an α adrenergic receptor agonist (combo).

DETAILED DESCRIPTION OF THE ILLUSTRATED EMBODIMENTS

Reference will now be made in detail to embodiments of the present invention, example of which is illustrated.

Anti-angiogenesis drugs and α-adrenergic receptors agonists are two types of agents known to affect blood vessels through different mechanisms.

Anti-angiogenic agents can have profound effects on blood vessel growth and can be used to reduce neovascularization and hyperemia. The anti-VEGF antibody ranibizumab inhibits vessel leakage, endothelial cell proliferation and new vessel formation. Anti-VEGF agents can also be used to reduce inflammation-induced redness (Peyman 2007). The VEGF signaling pathway can be blocked by targeting either the growth factor, VEGF or its receptors, VEGFRs. For example, in a rabbit corneal vascularization models, both an anti-VEGF antibody and a small molecule MKI against VEGFRs substantially reduced vascularity and hyperemia in the eye (Perez-Santonja et al. 2010; Ko et al. 2013; Ni 2017). In a pterygium model, an MKI against VEGFRs substantially reduced pterygium associated vascularity and hyperemia (Ni 2017). Anti-angiogenic agents that indirectly inhibit the VEGF signaling should also have the same effects on ocular hyperemia.

Vasoconstrictors, such as Naphazoline, can counter vessel dilation and thus reduce hyperemia (Cronau et al. 2010). Topical α-adrenergic receptor agonists such as brimonidine is used to reduce persistent facial redness in rosacea by constricting dermal blood vessels (Graeber et al. 2013). For hyperemia that doesn't have prominent vessel dilation as a factor, α-adrenergic receptor agonists can face the problem of rebound hyperemia when the redness exceeds the pre-treatment levels due to loss of drug effects (Horn 2010; Torkildsen et al. 2018). For example, one of the major side effects of the brimonidine formulation for glaucoma is hyperemia (Cantor 2006). One potential way to counter the rebound hyperemia problem is to use very low doses of α2 selective agonists (Horn 2010; Torkildsen et al. 2018). The effect of α-adrenergic receptor agonists on hyperemia is acute, with immediate onset of effect upon drug exposure and rapid loss of effect when drug is depleted.

The present invention provides a composition for use in the treatment of ocular hyperemia. The composition includes an anti-angiogenic agent and an α adrenergic receptor agonist. The anti-angiogenic agent can be an MKI that inhibits VEGFR 1, 2, and/or 3.

The MKI can be, for example, afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, linifanib, motesanib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, or vemurafenib; and the MKI is preferably nintedanib or axitinib.

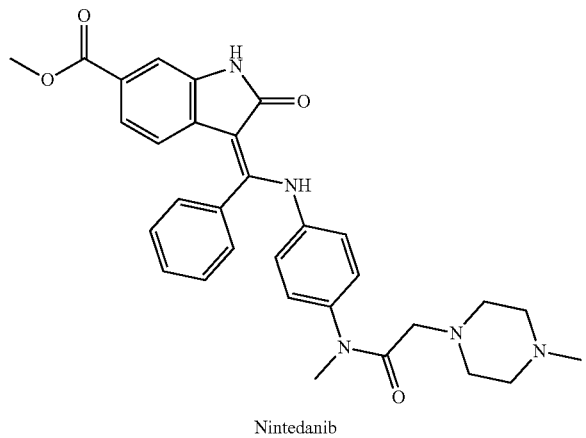

Nintedanib

The chemical name of nintedanib is (Z)-3-(1-(4-(N-((4-methyl-piperazin-1-yl)-methylcarbonyl)-N-methyl-amino)-phenylamino)-1-phenyl-methylene]-6-methoxycarbonyl-2-indolinone.

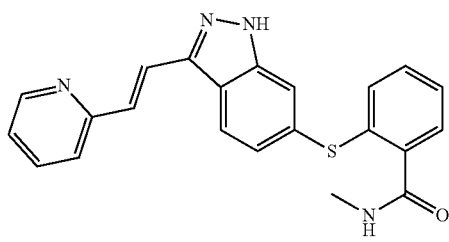

Axitinib

The chemical name of axitinib is N-methyl-2-[[3-[(E)-2-pyridin-2-ylethenyl]-1H-indazol-6-yl]sulfanyl]benzamide.

The anti-angiogenic agent can also be a biological agent that binds to VEGF to block the signal transduction of VEGF. The biological agent can be, for example, bevacizumab, ranibizumab, ramucirumab, aflibercept, or conbercept.

The α adrenergic receptor agonist can be naphazoline, tetrahydrozoline, oxymetazoline, methoxamine, phenylephrine, xylometazoline, oxedrine, Apraclonidine, mivaZerol, clonidine, brimonidine, alpha methyl dopa, guanfacine, dexemeditomidine, (+)-(S)-4-1-(2,3-dimethyl-phenyl)-ethyl-1,3-dihydro-imidazole-2-thione, 1-(imidazolidin-2-yl)iminolindazole, methoxamine, phenylephrine, tizanidine, xylazine, guanabenz, or amitraz.

The α adrenergic receptor agonist can also be a α2-adrenergic receptor agonist that is selective for α2-adrenergic receptors. The α2-adrenergic receptor agonist can be for example, brimonidine, apraclonidine, mivaZerol, clonidine, alpha methyl dopa, guanfacine, dexemeditomidine, (+)-(S)-4-1-(2,3-dimethyl-phenyl)-ethyl-1,3-dihydro-imidazole-2-thione, 1-(imidazolidin-2-yl)iminolindazole, methoxamine, phenylephrine, tizanidine, xylazine, guanabenz, or amitraz; and the α2-adrenergic receptor agonist is preferably brimonidine

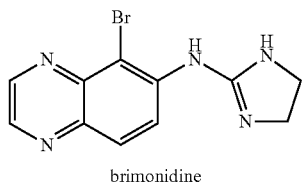 [SMILES: Brc1c(NC2=NCCN2)ccc2nccnc12]

brimonidine

The chemical name of brimonidine is (5-Bromoquinoxalin-6-yl)-(4,5-dihydro-1H-imidazol-2-yl)-amine.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, NY). For example, solutions, suspensions, creams, ointments, Gels, gel-forming liquid, suspension containing liposomes or micelles, spray formulation, or emulsions used for ophthalmic application can include the following components: a sterile diluent such as water for injection, saline solution, fixed oils, polyethylene glycols, glycerin, propylene glycol or other synthetic solvents; antibacterial agents; antioxidants; chelating agents; buffers such as acetates, citrates or phosphates and agents for the adjustment of tonicity such as sodium chloride or dextrose. The pH can be adjusted with acids or bases, such as hydrochloric acid or sodium hydroxide.

Pharmaceutical compositions suitable for injectable use can include sterile aqueous solutions (where water soluble) or dispersions and sterile powders for the extemporaneous preparation of sterile injectable solutions or dispersion. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

A topical ocular formulation is a solution, a suspension, creams, ointments, gels, gel-forming liquid, suspension containing liposomes or micelles, spray formulation, or an emulsion. In some cases, the topical ocular formulation also includes one or more pharmaceutically acceptable excipients selected from stabilizers, surfactants, polymer base carriers, gelling agents, organic co-solvents, pH active components, osmotic active components and with or without preservatives. In some cases, the sustained release semi-solid formulation, sustained release solid formulation or ocular implant is injected into the affected eye. In some embodiments, the sustained release semi-solid formulation, sustained release solid formulation or ocular implant further comprises a pharmaceutically acceptable excipient. In some cases, the sustained release semi-solid formulation, sustained release solid formulation or ocular implant includes a multikinase inhibitor, the antimetabolite, or combination thereof; and a biodegradable polymer selected from polylactic acid (PLA), poly lactic-co-glycolic acid (PLGA) and polylactic acid poly lactic-co-glycolic acid copolymers.

The composition for use in the treatment of ocular hyperemia can be an aqueous solution, a suspension, an emulsion or others. The composition can include 0.001%-1% (by weight based on the total weight of the composition) nintedanib and 0.001%-1% brimonidine; preferably 0.01%-0.5% nintedanib and 0.01%-0.5% brimonidine; preferably 0.1%-0.3% nintedanib and 0.01%-0.05% brimonidine; more preferably 0.2% nintedanib and 0.025% brimonidine.

As used herein, "an emulsion" is a translucent to transparent composition having a droplet size of 0.005 to 0.5 μm, thermodynamically stable and generally self emulsifying, and "a suspension" is a coarse dispersion in which internal phase (active ingredient) is dispersed uniformly throughout the external phase.

The present invention also provides a method for treating ocular hyperemia for a patient. The method includes both inhibiting VEGFR 1, 2, or 3 of the patient; and activating α adrenergic receptor of the patient.

VEGFR 1, 2, or 3 can be inhibited by administering an anti-angiogenic agent. The anti-angiogenic agent can be afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, linifanib, motesanib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, and vemurafenib; and the anti-angiogenic agent is preferably nintedanib.

The α-adrenergic receptor can be activated by administering an α adrenergic receptor agonist. The α adrenergic receptor agonist can be brimonidine, apraclonidine, mivaZerol, clonidine, alpha methyl dopa, guanfacine, dexemeditomidine, (+)-(S)-4-1-(2,3-dimethyl-phenyl)-ethyl-1,3-dihydro-imidazole-2-thione, 1-(imidazolidin-2-yl)iminolindazole, methoxamine, phenylephrine, tizanidine, xylazine, guanabenz, or amitraz; and the α-adrenergic receptor agonist is preferably brimonidine.

As shown in FIG. 1, when an ocular hyperemia patient is treated with an anti-angiogenic agent alone, vascularity and vessel leakage are reduced. When an ocular hyperemia patient is treated with an α-adrenergic receptor agonist alone, dilation is reduced. When an ocular hyperemia patient is treated with combo of an anti-angiogenic agent and an α-adrenergic receptor agonist, there are synergistic or additive effects on hyperemia.

Example 1: Synthesis of (Z)-3-(1-(4-(N-((4-methyl-piperazin-1-yl)-methylcarbonyl)-N-methyl-amino)-phenylamino)-1-phenyl-methylene]-6-methoxycarbonyl-2-indolinone (nintedanib)

Z)-3-(1-(4-(N-((4-methyl-piperazin-1-yl)-methylcarbonyl)-N-methyl-amino)-phenylamino)-1-phenyl-methylene]-6-methoxycarbonyl-2-indolinone is prepared by the method of synthesizing compound 473 described in PCT application publication no. WO 01/27081 A1.

Example 2: Synthesis of (5-Bromoquinoxalin-6-yl)-(4,5-dihydro-1H-imidazol-2-yl)-amine (brimonidine)

6-amino-5-bromoquinoxaline hydrobromide (10 g) is added to thiophosgene (3 ml) and distilled water (150 ml) while stirring. The mixture is reacted for two hours at room temperature and the resultant precipitate is filtered, washed with water, and dried to give 5-bromo-6-isothiocyanato-quinoxaline (3.6 g).

5-bromo-6-isothiocyanato-quinoxaline is dissolved in benzene (400 ml) and added drop-wise to a solution of ethylene diamine (15 g) in benzene (50 ml). The mixture is stirred for two hours, and an oil substrate separates as a lower layer. The upper benzene layer is discarded, and the oil is washed with diethyl ether and dissolved in methanol (500 ml). The methanol solution is refluxed to remove hydrogen sulfide. The methanol solution is then concentrated to a volume of about 100 ml, and a yellow solid then precipitates. The precipitate is collected by filtration and recrystallized from methanol to obtain (5-Bromo-quinoxalin-6-yl)-(4,5-dihydro-1H-imidazol-2-yl)-amine.

Example 3: Formulations

Vehicle emulsion formulation: this formulation contains the following inactive ingredients: hydroxypropyl guar, xantham gum, and trehalose or additional sugar molecules and derivatives.

0.2% Nintedanib emulsion formulation: this formulation contains 0.2% by weight nintedanib as active ingredient and the following inactive ingredients: hydroxypropyl guar, xantham gum, and trehalose or additional sugar molecules and derivatives.

0.025% brimonidine emulsion formulation: this formulation contains 0.025% by weight brimonidine as active ingredient and the following inactive ingredients: hydroxypropyl guar, xantham gum, and trehalose or additional sugar molecules and derivatives.

0.2% Nintedanib and 0.025% brimonidine emulsion formulation (combo-1): this formulation contains 0.2% by weight nintedanib and 0.025% brimonidine as active ingredient and the following inactive ingredients: hydroxypropyl guar, xantham gum, and trehalose or additional sugar molecules and derivatives.

0.1% Nintedanib and 0.015% brimonidine emulsion formulation (combo-2): this formulation contains 0.1% by weight nintedanib and 0.015% brimonidine as active ingredient and the following inactive ingredients: hydroxypropyl guar, xantham gum, and trehalose or additional sugar molecules and derivatives.

Example 4: Ocular Hyperemia

Treatments

Ocular hyperemia patients with hyperemia grade >2 (0-4, five-point scale; 0 being clear of hyperemia and 4 being of severe hyperemia) are selected for treatment with 4 emulsion formulations. Each group has about 20 patients. The patients are assigned to the groups in a way to make sure the base line average grade is similar among the groups. The formulations are dosed twice a day (BID) for 2 weeks and the patients are further followed up for 4 weeks. The formulations are administered topically by a physician on the day of visits or by the patient between visits. Patients are evaluated on day 1, week 1, and 2, before and after dosing. After the stop of dosing, patients are further followed up at 4 and 6 weeks.

Endpoints

The effect on ocular hyperemia is evaluated by taking pictures of the eye. The hyperemia is graded by an independent grader who does not know the treatments received by the eyes. The tolerability of the formulations is also evaluated with standard eye examinations commonly used for such assessment. The efficacy and tolerability data are analyzed by independent statisticians.

Results

For the vehicle group, the hyperemia grade had no significant changes from the baseline at any of the visits. For the nintedanib group, comparing to the baseline, the hyperemia grade did not change significantly on day 1. It was reduced about 1 grade at week 1 and 2. The grade reduction remained significant for 2 additional weeks after the stop of dosing For the brimonidine group, the hyperemia grade reduced immediately after dosing on day 1, week 1 and 2. The effect lasts about 2-4 hours at each of the visits. After stop of treatments, at week 4 and 6, the grade is the same as the baseline. For the combo group, the day 1 drug effect on hyperemia was similar to that of the brimonidine group on day 1 but the reduction was more than the single groups at weeks 1, 2, 4. A small but significant reduction of hyperemia still maintained at week 6. The combo-2, with half of the concentration, was still better than the single treatments. The effects on hyperemia grade are shown in Table 1 below.

No serious adverse effects and unacceptable adverse effects are observed in any of the groups.

TABLE 1

Average Hyperemia Grade for Each Group

|  | Vehicle | 0.2% Nintedanib | 0.025% Brimonidine | Combo-1 | Combo-2 |
| --- | --- | --- | --- | --- | --- |
| Day 1 before | 3 | 3 | 3 | 3 | 3 |
| Day 1 2 h post | 3 | 3 | 2 | 2 | 2.5 |
| Day 1 6 h post | 3 | 3 | 3 | 3 | 3 |
| Week 1 before | 3 | 2 | 3 | 2 | 2 |
| Week 1 2 h post | 3 | 2 | 2 | 1.5 | 2 |
| Week 2 before | 3 | 2 | 3 | 1.5 | 2 |
| Week 2 2 h post | 3 | 2 | 2 | 1 | 1.5 |
| Wee 4 | 3 | 2.5 | 3 | 2 | 2.5 |
| Week 6 | 3 | 3 | 3 | 2.5 | 3 |

Example 5: Nintedanib Effectively Reduced Vascularity in Pterygium Patients

Pterygium is an ocular surface disease characterized with abnormal fibrovascular tissue growth. Hyperemia due to excess neovascularization is a prominent feature of the disease.

Nintedanib was formulated into an eye drop and tested in pterygium patients in a Phase 2a clinical trial to evaluate the safety and efficacy of nintedanib. The key efficacy endpoint is effects on pterygium vascularity.

The clinic trial was conducted in two stages. In stage 1, the safety, tolerability and pharmacokinetics were evaluated in a single dose escalating study. Three dose cohorts with 8 patients in each were evaluated. Cohort 1 began at the lowest concentration of 0.02% nintedanib (weight percent based on the total weight of the eye drop), followed by an increasing dose to 0.05% for Cohort 2 and then to 0.2% for Cohort 3. No safety issues were found at all doses so the highest dose of 0.2% was chosen for stage 2.

In stage 2, the safety, tolerability and efficacy of the 0.2% formulation were evaluated in a randomized, double-masked, vehicle-controlled, parallel study with 28 days TID repeat ocular dosing of vehicle and 0.2% nintedanib. The patients were further followed up by 20 weeks of post-dosing observation. Ophthalmic and physical examinations were performed at screening, Day 1 and Week 2, 4, 8, 16, and 24. External photograph of the pterygium eye was taken using a digital camera and the pterygium vascularity was graded from these images at an independent image reading center. The primary objective is to evaluate ocular and systemic safety of nintedanib in pterygium patients that have moderate to severe pterygium vascularity. The secondary objective is to assess whether the formulation is efficacious in reducing pterygium vascularity.

A total of 50 patients were enrolled and randomized in a 1:1 treatment allocation to receive either nintedanib or vehicle. The final analysis was performed after study completion. The O'Brien-Fleming group-sequential method was used for a multiple-comparison adjustment of p-values for efficacy. For the final analysis, a 2-sided test with p-value ≤0.048 is considered statistically significant for all between and within treatment comparisons.

The safety and tolerability of the nintedanib formulation was excellent with no serious adverse events and some acceptable adverse events commonly associated with eye drops. The effect on pterygium vascularity was highly significant by Week 2 and the effects maintained through Week 16, 2 months after dosing had stopped. The results are summarized in Table 2 that shows the mean grade difference and the change from baseline difference between drug and vehicle groups.

This example demonstrated the potent effect of nintedanib on abnormal vascularity and hyperemia in pterygium patients. It is expected that when the nintedanib formulation is replaced with the combo-1 and combo-2 formulations, superior and synergistic effects will be achieved on reducing hyperemia in pterygium patients.

TABLE 2

Nintedanib Effectively Reduced Vascularity in Pterygium Patients

| | Nintedanib vs vehicle differences | | | |
| --- | --- | --- | --- | --- |
| | Mean grade | | Mean change from baseline | |
| | Difference | P value | Difference | P value |
| Day 1 (baseline) | −0.15 | 0.492 | NA | NA |
| Week 2 | −0.87 | 0.001 | −0.72 | 0.0000 |
| Week 4 (end of dosing) | −0.91 | 0.0002 | −0.76 | 0.0004 |
| Week 8 | −0.53 | 0.0143 | −0.41 | 0.0084 |
| Week 16 | −0.7 | 0.0017 | −0.59 | 0.0006 |
| Week 24 (end of study) | −0.31 | 0.1153 | −0.17 | 0.2661 |

REFERENCES

Cantor L B. Brimonidine in the treatment of glaucoma and ocular hypertension. Ther Clin Risk Manag. 2006 December; 2(4):337-46.

Cronau H, Kankanala R R, Mauger T. Diagnosis and management of red eye in primary care. Am Fam Physician. 2010 Jan. 15; 81(2):137-44.

Graeber M., Loesche C., Freidenreich P., Liu Y., Leoni M. J. METHODS AND COMPOSITIONS FOR SAFE AND EFFECTIVE TREATMENT OF ERYTHEMA. Patent US00851.3247B2. 2013.

Horn G. COMPOSITIONS AND METHODS FOR REVERSING REBOUND HYPEREMA. Patent US 2010.00296.60A1. 2010.

Ko B Y, Kim Y S, Baek S G, Lee G W, Kim J M, Jean W S, Lee N S, Kang J. Inhibition of corneal neovascularization by subconjunctival and topical bevacizumab and sunitinib in a rabbit model. Cornea. 2013; 32(5):689-695.

LUCENTIS (ranibizumab injection), package insert. South San Francisco, CA: Genentech, Inc; 2014

Ni J. COMPOSITIONS AND METHODS FOR TREATING PTERYGUM. Patent application US 2017/0209368 A1. 2017

Perez-Santonja J J, Campos-Mollo E, Lledo-Riquelme M, Javaloy J, Alio J. Inhibition of corneal neovascularization by topical bevacizumab (Anti-VEGF) and sunitinib (Anti-VEGF and Anti-PDGF) in an animal model. Am J Ophthalmol. 2010; 150(4):519-528.

Peyman G. A. Use of an anti-vascular endothelial growth factor (vegf) agent to ameliorate inflammation. Patent WO 2007038453 A2. 2007.

Torkildsen G L, Sanfilippo C M, DeCory H H, Gomes P J. Evaluation of Efficacy and Safety of Brimonidine Tartrate Ophthalmic Solution, 0.025% for Treatment of Ocular Redness. Curr Eye Res. 2018 January; 43(1):43-51.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method for treating ocular hyperemia in a patient comprising administering to an affected eye of the patient (a) a multi-kinase inhibitor (MKI) that inhibits one or more kinase receptors selected from Vascular Endothelial Growth Factor Receptors (VEGFR) 1, 2, and 3, platelet-derived growth factor receptors (PDGFR) α and β, and Lyn, and (b) an α adrenergic receptor agonist.

2. The method of claim 1, wherein the MKI is selected from the group consisting of afatinib, amuvatinib, axitinib, cabozantinib, canertinib, cediranib, ceritinib, crenolanib, crizotinib, dabrafenib, dacomitinib, dasatinib, erlotinib, foretinib, gefitinib, golvatinib, ibrutinib, icotinib, idelalisib, imatinib, lapatinib, lenvatinib, linifanib, motesanib, neratinib, nilotinib, nintedanib, palbociclib, pazopanib, ponatinib, quizartinib, regorafenib, ruxolitinib, sorafenib, sunitinib, tandutinib, tivantinib, tivozanib, trametinib, vandetanib, vatalanib, and vemurafenib; and wherein the α adrenergic receptor agonist is selected from the group consisting of naphazoline, tetrahydrozoline, oxymetazoline, methoxamine, phenylephrine, xylometazoline, oxedrine, Apraclonidine, mivaZerol, clonidine, brimonidine, alpha methyl dopa, guanfacine, dexemeditomidine, (+)-(S)-4-1-(2,3-dimethyl-phenyl)-ethyl-1,3-dihydro-imidazole-2-thione, 1-(imidazolidin-2-yl)iminolindazole, methoxamine, phenylephrine, tizanidine, xylazine, guanabenz, and amitraz.

3. The method of claim 1, wherein the MKI and the α adrenergic receptor agonist are administered to the affected eye in the form of a topical ocular formulation, an ointment, a gel, a sustained release semi-solid formulation, a sustained release solid formulation or an ocular implant.

4. The method of claim 3, wherein the sustained release semi-solid formulation, the sustained release solid formulation, or the ocular implant is injected into the affected eye.

5. The method of claim 1, wherein the MKI is nintedanib or axitinib.

6. The method of claim 1, wherein the α adrenergic receptor agonist is brimonidine.

7. The method of claim 1, comprising administering a composition comprising 0.001%-1% (w/w) nintedanib and 0.001%-1% (w/w) brimonidine.

* * * * *